(12) United States Patent
Lewis

(10) Patent No.: US 7,541,146 B2
(45) Date of Patent: *Jun. 2, 2009

(54) BIOMOLECULE RETAINING MATERIAL AND METHODS FOR ATTACHING BIOMOLECULES TO A SURFACE

(75) Inventor: Mark A. Lewis, Corning, NY (US)

(73) Assignee: Corning Incorporated, Corning, NY (US)

(*) Notice: Subject to any disclaimer, the term of this patent is extended or adjusted under 35 U.S.C. 154(b) by 110 days.

This patent is subject to a terminal disclaimer.

(21) Appl. No.: 11/488,557

(22) Filed: Jul. 18, 2006

(65) Prior Publication Data

US 2006/0257920 A1  Nov. 16, 2006

Related U.S. Application Data

(63) Continuation of application No. 10/277,565, filed on Oct. 21, 2002, now abandoned.

(51) Int. Cl.
  *C12Q 1/68* (2006.01)
  *C12P 19/34* (2006.01)
  *C07H 21/04* (2006.01)

(52) U.S. Cl. .................. 435/6; 435/91.1; 435/91.2; 536/24.3; 536/24.33

(58) Field of Classification Search .............. None
See application file for complete search history.

(56) References Cited

U.S. PATENT DOCUMENTS

| | | | |
|---|---|---|---|
| 4,141,857 A | 2/1979 | Levy et al. | 502/439 |
| 4,529,618 A | 7/1985 | Ponjee et al. | 435/176 |
| 4,581,336 A | 4/1986 | Malloy et al. | 435/176 |
| 5,087,522 A | 2/1992 | Bailly et al. | 428/402 |
| 5,474,796 A | 12/1995 | Brennan | 427/2.13 |
| 5,510,270 A | 4/1996 | Fodor et al. | 436/518 |
| 5,688,642 A | 11/1997 | Chrisey et al. | 435/6 |
| 5,728,588 A | 3/1998 | Caldwell et al. | 436/532 |
| 5,858,653 A | 1/1999 | Duran | 435/6 |
| 5,959,098 A | 9/1999 | Goldberg et al. | 536/25.3 |
| 6,159,695 A | 12/2000 | McGovern et al. | 435/6 |
| 6,548,264 B1 | 4/2003 | Tan et al. | 435/7.21 |
| 6,750,023 B2 | 6/2004 | Tanner et al. | 435/6 |
| 7,195,908 B2 * | 3/2007 | Lewis | 435/285.2 |
| 2003/0054176 A1 | 3/2003 | Pantano et al. | 428/429 |
| 2003/0059819 A1 | 3/2003 | Tzeng et al. | 435/6 |
| 2003/0099930 A1 | 5/2003 | Graves et al. | |
| 2004/0076961 A1 | 4/2004 | Lewis | 435/6 |
| 2004/0086939 A1 | 5/2004 | Hancock, Jr. et al. | 435/7.1 |
| 2004/0146460 A1 | 7/2004 | Salafsky | |

FOREIGN PATENT DOCUMENTS

WO    WO 02/094573 A1 * 11/2002

OTHER PUBLICATIONS

Chrisey et al., "Covalent attachment of synthetic DNA to self-assembled monolayer films," Nucleic Acids Research, 1996, vol. 24, No. 15, pp. 3031-3039.*
Oh et al., "Characteristics of DNA Microarrays Fabricated on Various Aminosilane Layers," Langmuir 2002, pp. 1764-1769.*
Soon Jin Oh et al., "Characteristics of DNA Microarrays Fabricated on Various Aminosilane Layers", Langmuir 2002, vol. 18, pp. 1764-1769.
Advanced Organic Chemistry; Reactions, Mechanisms and Structure, Wiley, New York 1992, p. 1016.
Kazuyuki Hayashi et al., "Regulation of the Surface Potential of Silicon Substrates in Micrometer Scale with Organosilane Self-Assembled Monolayers", Langmuir 2002, vol. 18, pp. 7469-7472.
Linda A. Chrisey, Gil U. Lee, C. Elizabeth O'Ferrall, "Covalent Attachment of Synthetic DNA to Self-Assembled Movolayer Films", Nucleic Acids Research, 1996, vol. 24, No. 15, 3031-3039.
U.S. Appl. No. 11/027,318, filed Dec. 30, 2004, Entitled: Substrates Having Pendant Epoxide Groups for Binding Biomolecules and Methods of Making and Using Thereof.

* cited by examiner

*Primary Examiner*—Young J Kim
(74) *Attorney, Agent, or Firm*—Susan S. Wilks; Larry A. Villanueva; Joanne N. Pappas

(57) ABSTRACT

The present invention provides a method and material for attachment of biomolecules onto the surface of a substrate, such as microwell plates, tubes, beads, microscope slides, silicon wafers or membranes. The material includes a substrate having a surface coating including a polyamine compound. In one embodiment, the method and material are used to immobilize nucleic acid probes onto plastic materials such as microwell plates, e.g., for use in hybridization assays. In particular, the material can be used to attach a biomolecule (e.g., a nucleic acid) which in turn can be used for specific binding reactions (e.g., to hybridize a nucleic acid to its complementary strand).

30 Claims, 11 Drawing Sheets

General overalkylation of primary Amines

Compounds for the polyamino surface chemistry

R= Trialkoxysilyl

Trialkoxysilylpropyl ethylenediamine

Trialkoxysilylpropyl diethylenetriamine

Trialkoxysilylpropyl ethylenediamine

Glass Surface    R= alkyl

Glass Surface    R= H slide#511_boil(75-75)

slide#511(60-60)

Glass Surface  R=CH$_3$

Glass Surface  R=CH$_3$

Glass Surface  R=CH$_3$

Initial printing (70/70)

Following prehyb and boil (75/75)

Hyb channel 2 (80/80)

Hyb channel 1 (95/95)

Initial printing (70/70)

Following prehyb and boil (75/75)

Hyb channel 2 (80/80)

Hyb channel 1 (95/95)

Initial printing (70/70)

Following prehyb and boil (75/75)

Hyb channel 2 (80/80)

Hyb channel 1 (95/95)

Initial printing

Following boil test

BIOMOLECULE RETAINING MATERIAL AND METHODS FOR ATTACHING BIOMOLECULES TO A SURFACE

CROSS-REFERENCE TO RELATED APPLICATION

This application is a continuation of U.S. application Ser. No. 10/277,565, filed on Oct. 21, 2002 now abandoned the content of which is relied upon and incorporated herein by reference in its entirety, and the benefit of Priority under 35 U.S.C. § 120 is hereby claimed.

FIELD OF THE INVENTION

The present invention relates generally to a biomolecule retaining material and methods for attaching biomolecules, such as oligonucleotides, to a surface.

BACKGROUND OF THE INVENTION

A biological array can contain a chosen collection of biomolecules, for example, probes specific for important pathogens, sequence markers, antibodies, immunoglobulins, receptor proteins, peptides, cells, and the like. For example, an array can contain a chosen collection of oligonucleotides specific for known sequence markers of genetic diseases or probes to isolate a desired protein from a biological sample. A biological array may comprise a number of individual biomolecules tethered to the surface of a substrate in a regular pattern, each one in a different area, so that the location of the biomolecule is known.

Biological arrays can be synthesized directly on a substrate employing methods of: solid-phase chemical synthesis in combination with site-directing mass, as disclosed in U.S. Pat. No. 5,510,270, incorporated herein by reference in its entirety; photolithographic techniques involving precise drop deposition using piezoelectric pumps, as disclosed in U.S. Pat. No. 5,474,796, incorporated herein by reference in its entirety; or contacting a substrate with typographic pins holding droplets and using ink jet printing mechanisms to lay down an array matrix.

There are those who believe that generating a probe on a surface using methods of solid phase synthesis is a better process than attaching the final product to a modified surface. While this might avoid the complications of adding an anchor point (functionality added for the specific purpose of surface reaction), it produces the unavoidable consequence of any linear non-convergent synthesis which results in a low yield of the desired product. For example, a 10 step linear synthesis giving a 95% yield in each step gives a final yield of only 60%. The synthesis of a 20-mer gives a final yield of 36% and a 30-mer gives final yield of 21%. By the time a 50-mer is reached only 8% of the desired product is left. The other 92% are fragments left over during each synthesis step. An added complication is that each fragment may react in any subsequent synthetic step, which in turn generates any number of alternate sequences other than the desired one. This has the ultimate problem of producing false positives during the hybridization reaction. It would be ideal if each synthesis reaction could produce the 95% yield, which presently is not realistic because each step suffers some loss attributed to several factors which include, but are not limited to, bad reagents, wrong time and/or temperature, and contamination.

An example of a modified surface is an aldehyde surface that attaches to a primary amine to form the imine (Schiff Base), however, it requires the use of a hydride reducing agent to stabilize the bond. The reason the bond is unstable is that imines are susceptible to hydrolysis resulting in the amine and the aldehyde. Traditionally, the hydride reducing agent is a borohydride in a less reactive form like the cyanoborohydride. The purpose of the cyano group is to reduce the reactivity of the hydrides protons which immediately form $H_2$ in the presence of water and consume the reagent. A problem with using boron is that it forms stable complexes with amine functions that usually need rigorous conditions to break. Another problem with these reducing agents is that they react with many carbonyl groups of which an aldehyde is merely one example. Amides are another type of carbonyl group present in the bases thymine, cytosine, and guanine, which can also be attacked by hydride reagents.

Substrates are available for immobilization of biomolecules using either covalent attachment of biomolecules or non-covalent attachment of biomolecules. γ-aminopropylsilane (GAPS) is traditionally used as the surface of choice for the non-covalent binding of DNA (or other biomolecules) and has given the approach a degree of success. However, better retention and signal intensity would be desirable. In particular, there is some degradation observed with the primary amine surface (decreased signal in the gold colloid test). The nature of the primary amine degradation is not well understood but is believed to be a result of a reaction with $CO_2$ forming the carbamic acid salt or air oxidation. Further, there is an issue of whether the ammonium ions formed when using GAPS can then be covalently bonded to DNA during a UV exposure.

The present invention is directed to overcoming the above-noted deficiencies in the prior art.

SUMMARY OF THE INVENTION

The present invention provides a biomolecule retaining material including a substrate having a surface coating including a polyamine compound. The retaining material allows for non-covalent attachment of biomolecules (also referred to herein as target molecules and capture molecules), such as nucleic acids, onto the surface of the substrate. Suitable substrates include microwell plates, tubes, beads, microscope slides, silicon wafers, and membranes.

In one embodiment, the biomolecule retaining material is used to immobilize nucleic acid probes onto plastic materials such as microwell plates, e.g., for use in hybridization assays. In a preferred embodiment, the substrates are substantially flat surfaces, such as those provided by microscope slides and other plastic, silicon hydride, or organosilane-pretreated glass or silicone slide support surfaces.

In another embodiment, the present invention provides a method for treating a biomolecule retaining material. The method includes coating a substrate with a polyamine compound and treating the polyamine compound with an end capping reagent suitable to increase the water contact angle of the coated substrate.

In the material and method of the present invention, the use of polyamine surfaces increases the bond density of the surface, thus giving better retention, greater signal to noise ratio (S/N), and low background fluorescence. In particular, the use of polyamine compounds to coat the surface of the material increases the number of ammonium ions per molecule. Since the negatively charged phosphate backbone of DNA has an ion-ion (electrostatic) interaction with a positively charged ammonium ion surface, the increase in the number of ammonium ions per molecule gives a proportional increase in signal when DNA is the biomolecule of interest. Moreover, in accordance with the present invention, the use of multiple modes can be extended beyond the polar/ionic functionality of a biomolecule (e.g., phosphate of DNA) to include van der Waals interactions (e.g., interactions with the bases in DNA). In particular, in one embodiment of the present invention, the use of conjugated groups in the polyamine compound provides another mechanism to bind biomolecules to the retaining material in concert with the ionic and dipole interactions. In addition, the use of an end capping reagent in accordance with the method of the present invention provides a hydrophobic surface (e.g., a water contact angle of approximately 60-80°). A higher contact angle allows the formation of a more dense array (e.g., 40 K/slide or more).

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary. of the invention, and are intended to provide an overview or framework for understanding the nature and character of the invention as it is claimed.

BRIEF DESCRIPTION OF THE FIGURES

The accompanying drawings, which are incorporated in and constitute a part of this specification, illustrate embodiments of the invention and together with the description, serve to explain the objects, advantages, and principles of the invention.

(FIG. 5A), and denatured in boiling water for two minutes (FIG. 5B).

FIG. 7A shows the initial printing. FIG. 7B shows the slide following prehybridization and boiling. FIGS. 7C-D show hybridization.

FIG. 8A shows the initial printing. FIG. 8B shows the slide following prehybridization and boiling. FIGS. 8C-D show hybridization.

FIG. 9A and 9E show the initial printing. FIG. 9B shows the slide following prehybridization and boiling. FIGS. 9C-D show hybridization. FIG. 9F shows the slide following a boil test.

DETAILED DESCRIPTIION OF THE INVENTION

Figure 1A:
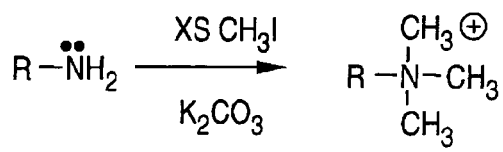
FIGS. 1A-B are a representation of a method of making an overalkylated biomolecule retaining material of the invention.
Figure 1A:
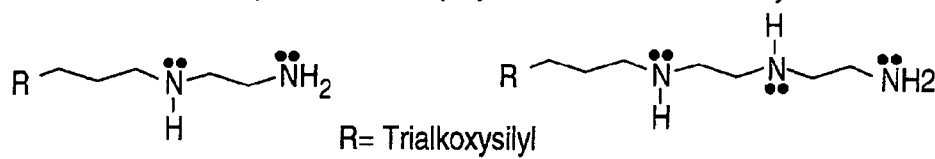
Figure 1A:
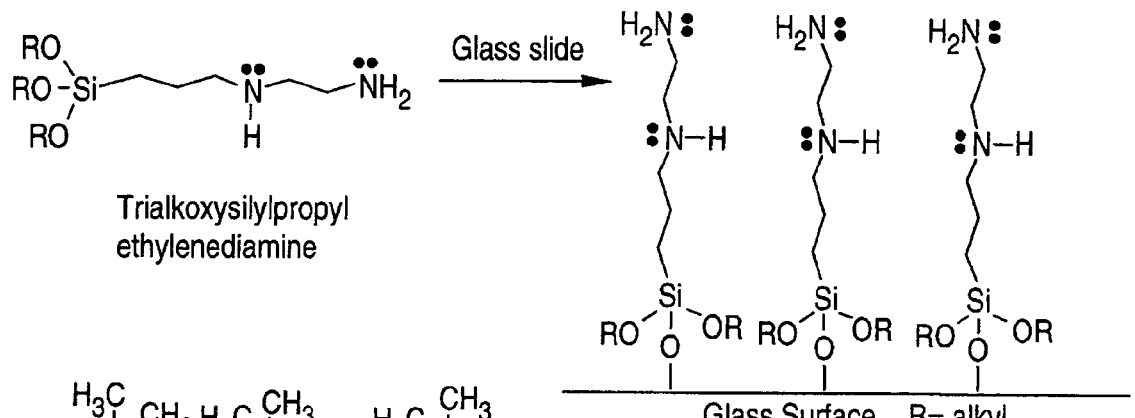
Figure 1A:
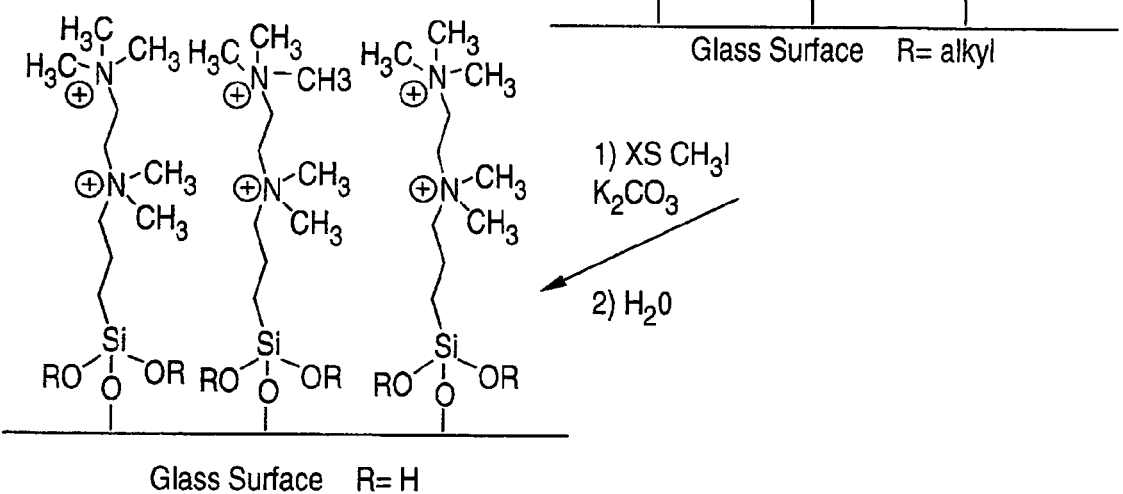
Figure 1B:
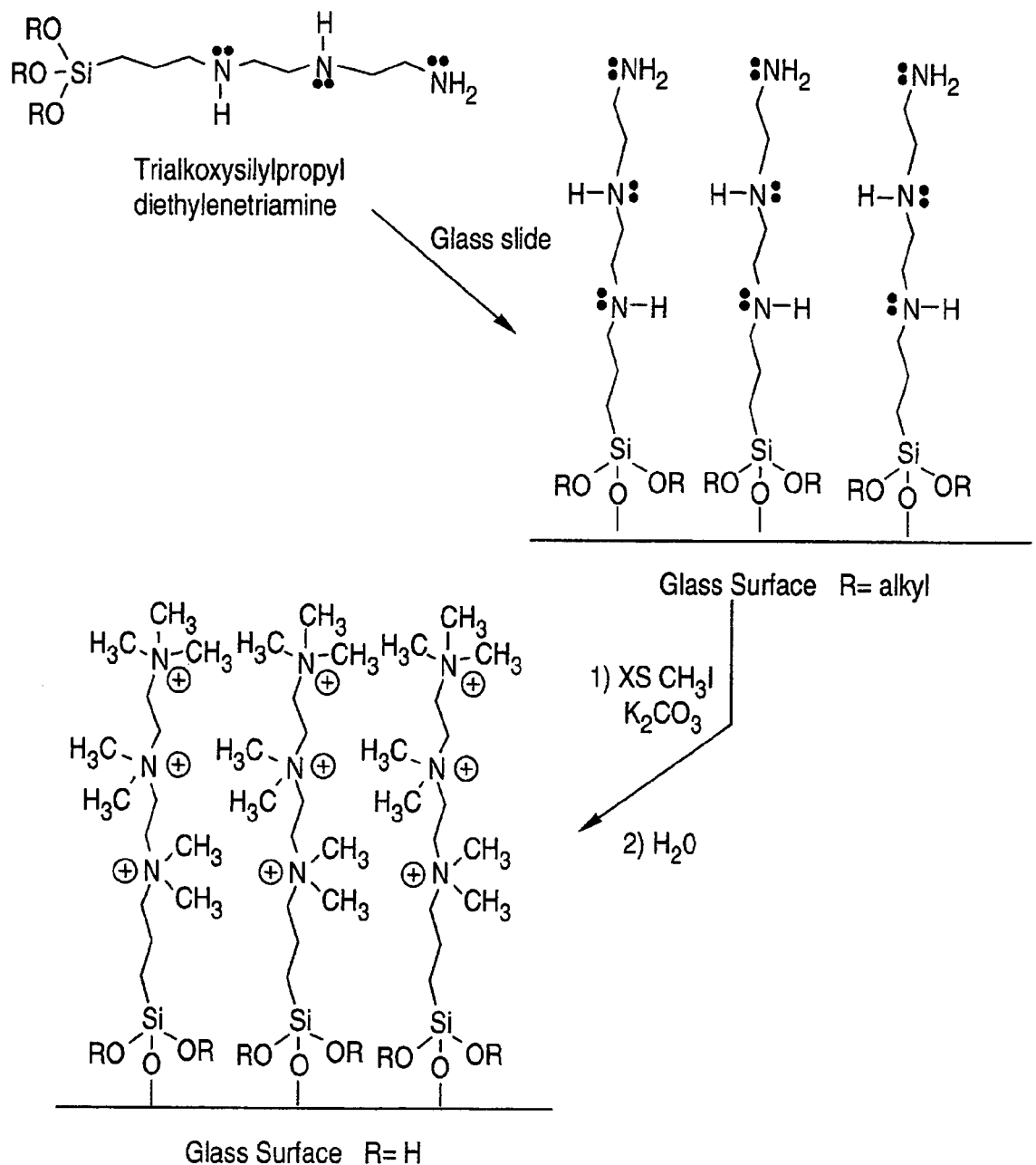

The present invention provides a biomolecule retaining material including a substrate having a surface coating including a polyamine compound. The coating including a polyamine compound may be present on all or a portion of a surface of the substrate. The retaining material allows for attachment of biomolecules (also referred to as target molecules and capture molecules) onto at least a portion of a surface of the substrate.

Suitable substrates include, but are not limited to, microwell plates, tubes, beads, microscope slides, silicon wafers, and membranes. Substrates can be prepared from a variety of materials, including but not limited to, glass and plastic materials selected from the group consisting of crystalline thermoplastics (e.g., high and low density polyethylenes, polypropylenes, acetal resins, nylons, and thermoplastic polyesters) and amorphous thermoplastics (e.g., polycarbonates and poly(methyl methacrylates)). Suitable plastic or glass materials provide a desired combination of such properties as rigidity, toughness, resistance to long term deformation, recovery from deformation on release of stress, and resistance to thermal degradation.

In one embodiment, the biomolecule retaining material is used to immobilize nucleic acid probes onto plastic materials such as microwell plates, e.g., for use in hybridization assays. In a preferred embodiment, the substrates are substantially flat surfaces, such as those provided by microscope slides and other plastic, silicon hydride, or organosilane-pretreated glass or silicone slide support surfaces.

Suitable polyamine compounds include, but are not limited to, diamines and triamines. In one embodiment, the polyamine compound comprises $(OR^1)_3Si$—$CH_2$$(CH_2CH_2NH)_n$—H, wherein n is an integer of two or greater and $R^1$ is hydrogen or a lower alkyl having from one to four carbon atoms. Preferably, n is from two to three.

In another embodiment, the polyamine compound comprises $(OR^1)_3Si$—$CH_2(CH_2CH_2NR^2)_n$—H, wherein n is an integer of two or greater, $R^1$ is hydrogen or a lower alkyl having from one to four carbon atoms, and $R^2$ is an alkyl, acyl, anhydride, ester, or other electrophilic species. In one particular embodiment, $R^1$ is methyl and $R^2$ is a trifluoroacetyl group. Preferably, n is from two to three.

In yet another embodiment, the polyamine compound comprises $(OR^1)_3Si$—$(CH_2)_n$—$R^2$—$(CH_2)_m$—NH—$(CH_2)_p NR^3H$, wherein $R^1$ is hydrogen or a lower alkyl having from one to four carbon atoms, $R^2$ is a methylene group or a conjugated group, $R^3$ is hydrogen or a conjugated group, provided that at least one of $R^2$ or $R^3$ is a conjugated group, n is an integer of one or greater, m is an integer of one or greater, and p is an integer of one or greater. Suitable conjugated groups include, but are not limited to, groups with multiple conjugated double bonds (e.g., aromatic groups and conjugated dienes), allylic carbocations, and allylic free radicals. Preferably, n, m, and p are integers from one to three.

In a further embodiment, the polyamine compound comprises $(OR^1)_3Si$—$(CH_2)_n$—NH—$(CH_2)_m$—$NH_2$, wherein $R^1$ is hydrogen or a lower alkyl having from one to four carbon atoms, n is an integer of one or greater, and m is an integer of one or greater. Preferably, n and m are integers from one to six.

Suitable examples of polyamine compounds include, but are not limited to, trialkoxysilylpropyl ethylenediamine, trialkoxysilylpropyl diethylenetriamine, (aminoethylaminomethyl)phenethyl trimethoxysilane, N-(6-aminohexyl)aminopropyl trimethoxysilane, and 3-(N-styrylmethyl-2-aminoethylamino)propyltrimethoxysilane (from the HCl salt). Due to the linear nature of these particular amines, they will form a layer of positive charge without the restrictions in movement that would occur in a polymeric structure. This allows the biomolecule to be immersed (embedded) into the surface coating, which results in better retention and subsequent signal intensity.

In one embodiment, at least one amine of the polyamine is alkylated. In yet another embodiment, the polyamine compound is over-alkylated. For example, the polyamine compound may be exhaustively methylated using methyl iodide (e.g. a 5% solution) or dimethyl carbonate, as shown in FIG. 1. In the method shown in FIG. 1, the polyamine compound is overalkylated after attachment to the substrate, however, the polyamine compound may be overalkylated prior to attachment to the substrate.

In further embodiments, at least one amine of the polyamine is reacted to prevent any subsequent bond formation with a biomolecule. This can be accomplished, for example, by overalkylating the at least one amine of the polyamine utilizing protecting groups (this also distinguishes a primary amine from the secondary amines).

Suitable biomolecules (i.e., target molecules or capture molecules) include, but are not limited to, plasmid DNA, cosmid DNA, bacteriophage DNA, genomic DNA (includes, but not limited to yeast, viral, bacterial, mammalian, and insect), RNA, cDNA, PNA, and oligonucleotides.

When preparing microarrays, biomolecules (e.g., oligonucleotides or cDNA, which are to be attached to the microarray surface) are generally delivered to the surface in a volume of less than about 1 nanoliter per spot, using printing pins adapted to form the spots into arrays having center to center spacing of about 200 µm to about 500 µm.

Given their small volumes, the printed arrays tend to dry quickly after exposure to the biomolecules, thus further affecting the coupling kinetics and efficiency. Unlike the coupling of DNA from solution and onto the surface of coated microplate wells, oligonucleotides printed in arrays of extremely small spot sizes tend to dry quickly, thereby altering the parameters affecting the manner in which the oligonucleotides contact and couple with the support. In addition to the design and handling of the printing pins, other factors can also affect the spot size, and in turn, the ultimate hybridization signals, including: salt concentrations, type of salts and wetting agents in the printing buffer, hydrophobic/hydrophilic properties of the surfaces; the size and/or concentration of the oligonucleotide; and the drying environments.

In a preferred embodiment, the polyamine compound can be used to prepare coated substrates (e.g., slides) having the compound bound thereto. The substrate can be stably stored and used at a later date to prepare microarrays.

Coated slides of the present invention are particularly well suited to replace conventional (e.g., silylated) glass slides in the preparation of microarrays using manufacturing and processing protocols, reagents, and equipment, such as microspotting robots (e.g., as available from Cartesian) and a chipmaker micro-spotting device (e.g., as available from TeleChem International). Suitable spotting equipment and protocols are commercially available, such as the "ArrayIt,"™ ChipMaker 3 spotting device.

The use of such an instrument, in combination with conventional (e.g., poly-l-lysine coated) slides, is well known in the art. See, for instance, U.S. Pat. No. 5,087,522 (Brown et al.) "Methods for Fabricating Microarrays of Biological Samples", and the references cited therein, the disclosures of each of which are incorporated herein by reference in their entirety.

For instance, the material of the present invention can be used to provide a substrate, such as a glass slide, with a surface having one or more microarrays. Each microarray preferably provides at least about $100/cm^2$ (and more preferably at least about $1000/cm^2$) of distinct biomolecules (e.g., polynucleotide or polypeptide biopolymers) in a surface area of less than about 1 $cm^2$. Each distinct biomolecule is preferably: (1) disposed at a separate, defined position in the array; (2) has a length of at least 10 subunits; (3) is present in a defined amount between about 0.1 femtomoles and about 10 nanomoles; and (4) is deposited in selected volume in the volume range of about 0.01 nanoliters to about 100 nanoliters. These regions (e.g., discrete spots) within the array can be generally circular in shape, with a typical diameter of between about 10 microns and about 500 microns (and preferably between about 20 and about 200 microns) or any other suitable shape. The regions are also preferably separated from other regions in the array by about the same distance (e.g., center to center spacing of about 20 microns to about 1000 microns).

The use of polyamine surfaces increases the bond density of the surface to give better retention, greater S/N, and low background fluorescence. The polyamine surfaces described above satisfy these requirements. However, it would be desirable to have a surface that provides all the aforementioned attributes as well as hydrophobic surface (water contact angle~60-80°). A higher contact angle will allow for a more dense array (40 K/slide or more) to be put on the same substrate.

Thus, another aspect of the present invention relates to a method for treating a biomolecule retaining material. The method includes coating a substrate with a polyamine compound and treating the polyamine compound with an end capping reagent suitable to increase the water contact angle of the coated substrate.

Techniques for coating the substrate with a polyamine compound are known in the art and are described, for example, in Oh et al., "Characteristics of DNA Microarrays Fabricated on Various Aminosilane Layers," *Langmuir*, 18:1764-1769 (2002), which is hereby incorporated by reference in its entirety.

Figure 2:
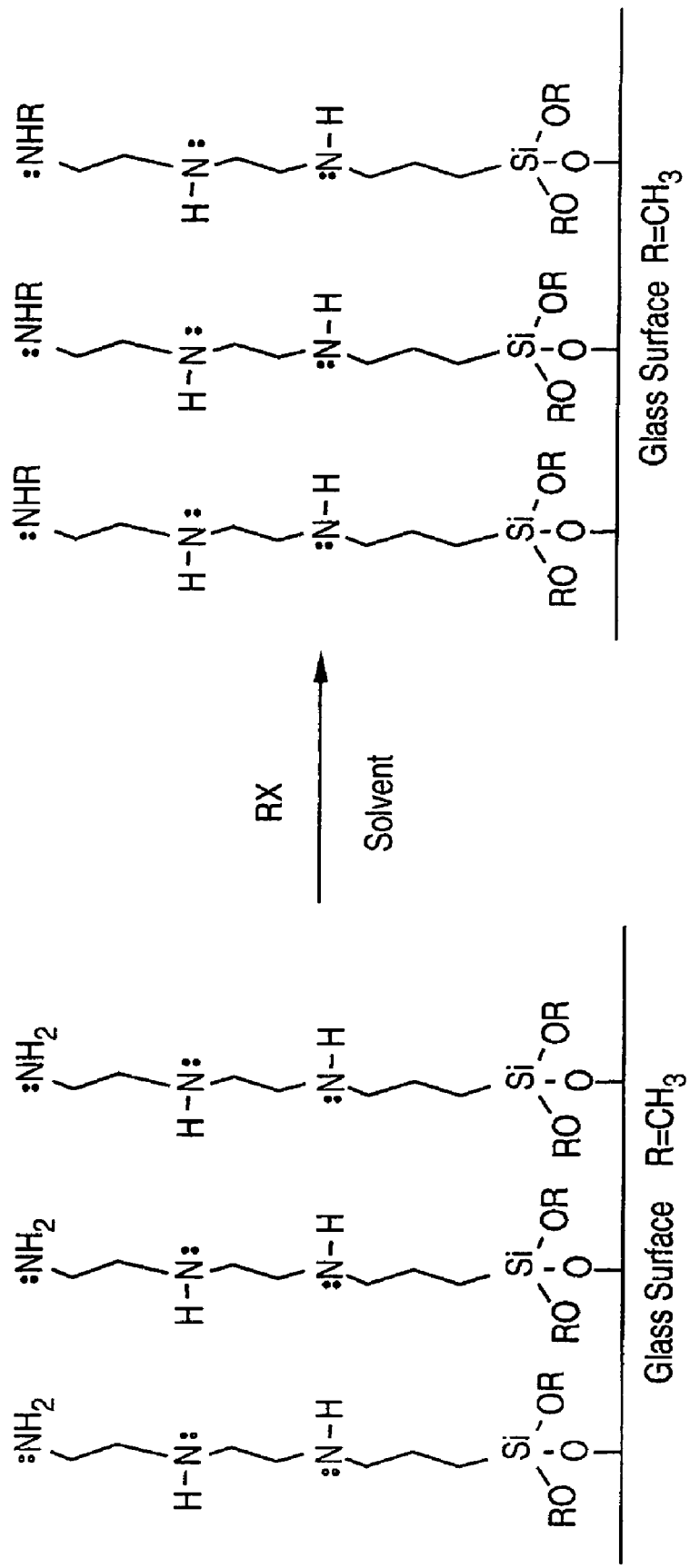
FIG. 2 is a schematic showing the reaction of a glass surface modified with trimethoxysilylpropyl diethylenetriamine with a compound that will impart hydrophobicity.
Figure 3A:
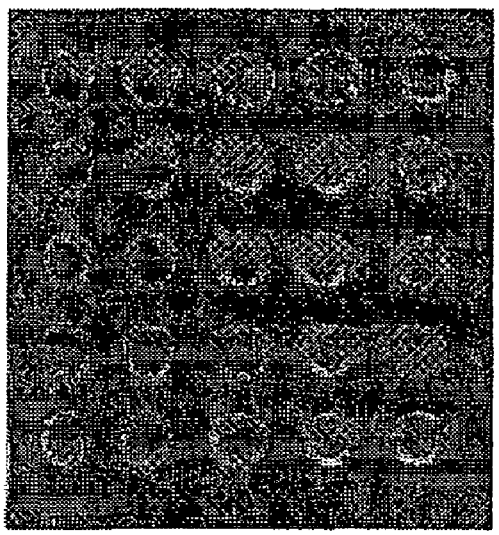
FIGS. 3A-D show glass slides coated with overalkylated trimethoxysilylpropyl ethylenediamine (FIGS. 3A and 3C) and denatured in boiling water for two minutes (FIGS. 3B and 3D).
Figure 3B:
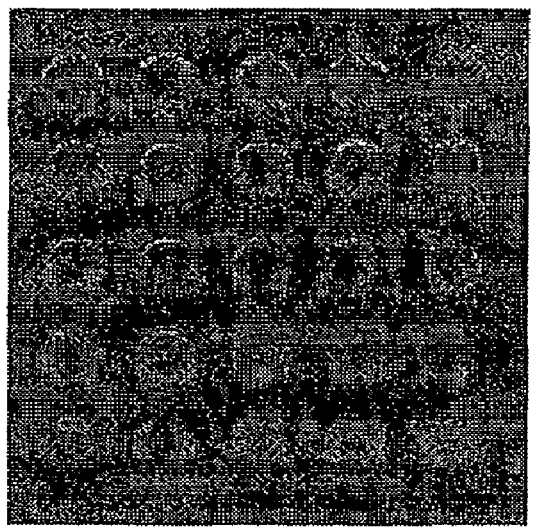
Figure 3C:
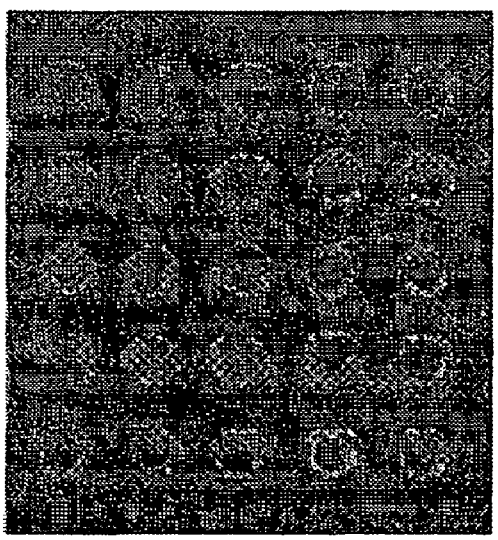
Figure 3D:
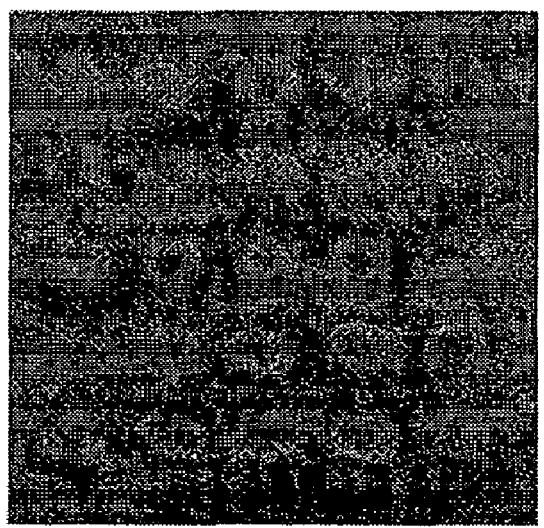
Figure 4A:
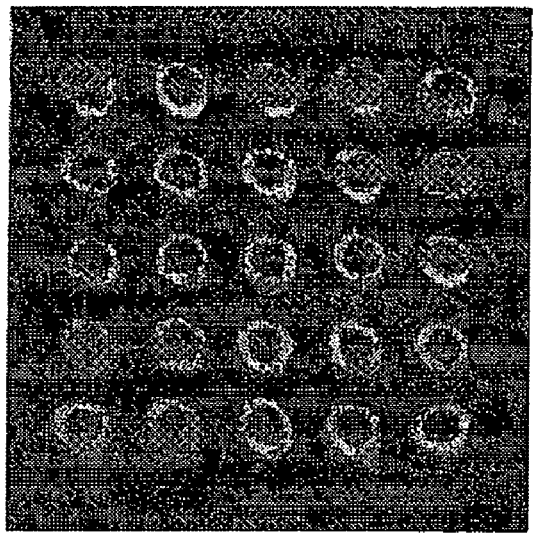
FIGS. 4A-D show glass slides coated with trimethoxysilylpropyl ethylenediamine (FIGS. 4A and 4C) and denatured in boiling water for two minutes (FIGS. 4B and 4D).
Figure 4B:
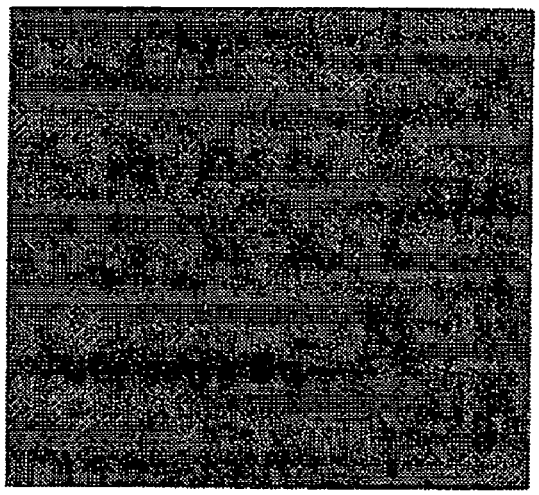
Figure 4C:
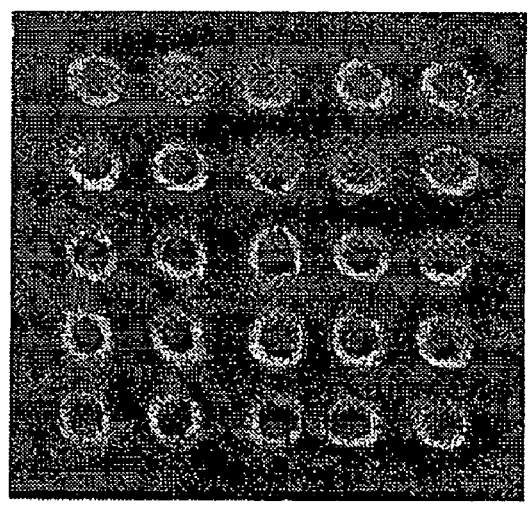
Figure 4D:
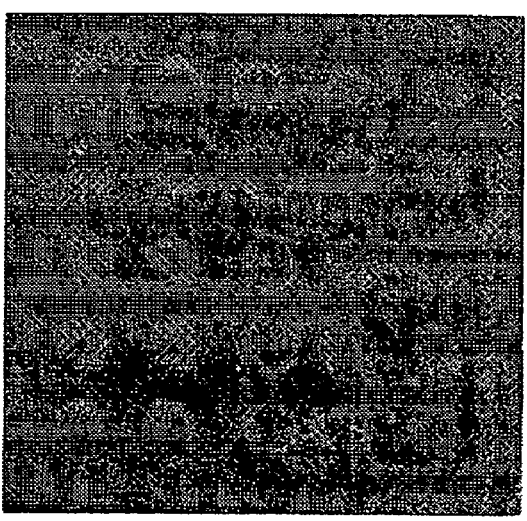

In accordance with the method of the present invention, the polyamine compound is treated with a end capping reagent. In particular, the treating comprises reacting the amine with a compound that will impart the desired hydrophobicity (i.e., the amine is treated with the appropriate reagent to essentially "end cap" the amine). FIG. 2 shows a form of the reaction in which the glass surface is already modified with the polyamine (e.g., triamine), however, the polyamine may be treated with the end capping reagent prior to attachment to the substrate. By choosing the proper group, the properties of the surface can be dramatically altered.

Suitable end capping reagents include, for example, alkyl halides, acyl halides, anhydrides, esters, combinations thereof, and any electrophilic reagent containing the desired pendant functionality. Preferably, the contact angle for the treated amino surface is greater than about 46°. More preferably, the end capping agent results in a coated substrate having a water contact angle of from about 50° to about 80°. Most preferably, the end capping agent results in a coated substrate having a water contact angle greater than about 70°. Thus, in accordance with the present invention, the amine surface can be modified in such a way tat gives a high contact angle without sacrificing the superior retention, S.N, and low background fluorescence of the biomolecule retaining material.

In one embodiment, the method preferably includes the step of alkylating or over-alkylating at least one amine, as shown in FIG. 1.

Figure 6A:
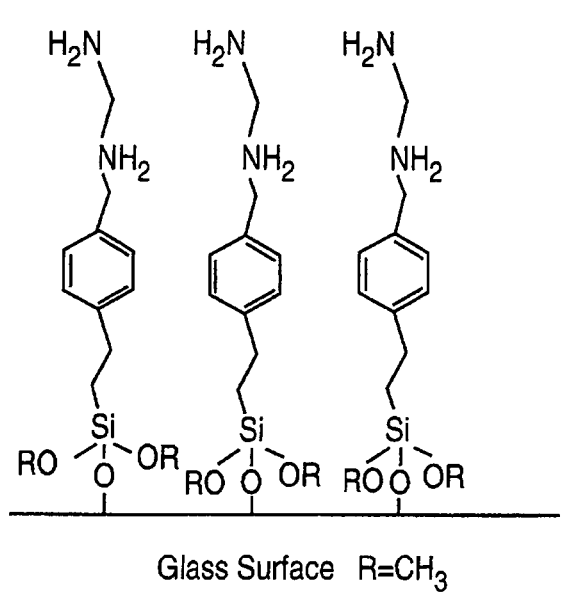
FIG. 6 shows three polyamino surfaces.
Figure 6B:
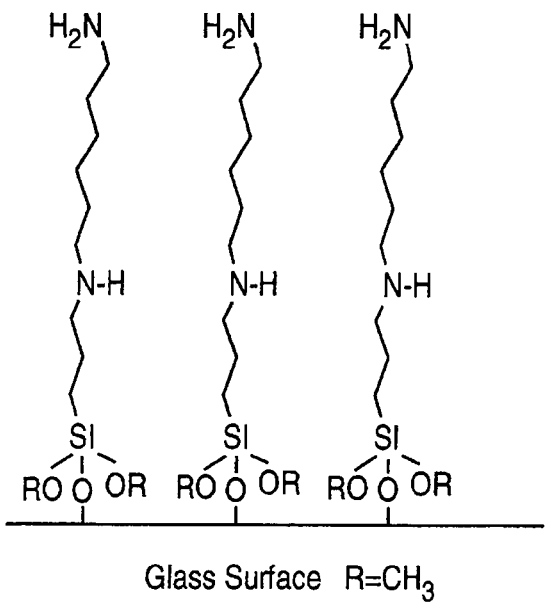
Figure 6C:
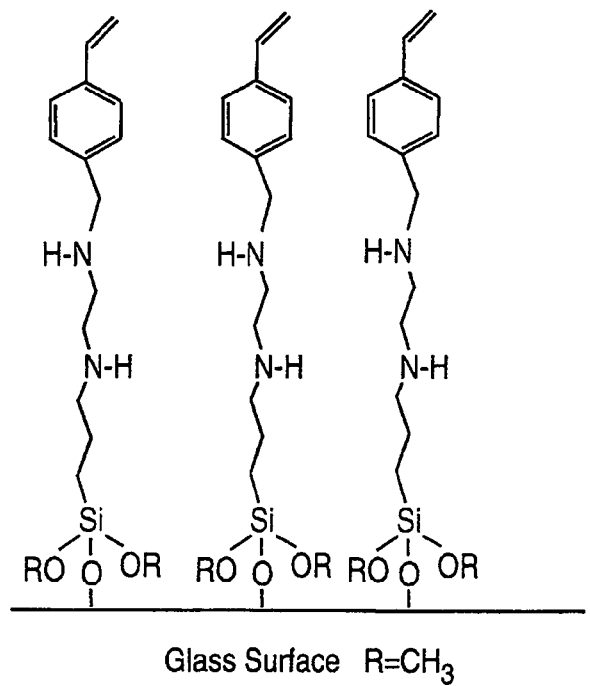
Figure 7A:
FIGS. 7A-D show a glass slide coated with (aminoethylaminomethyl)phenethyl trimethoxysilane.
Figure 7B:
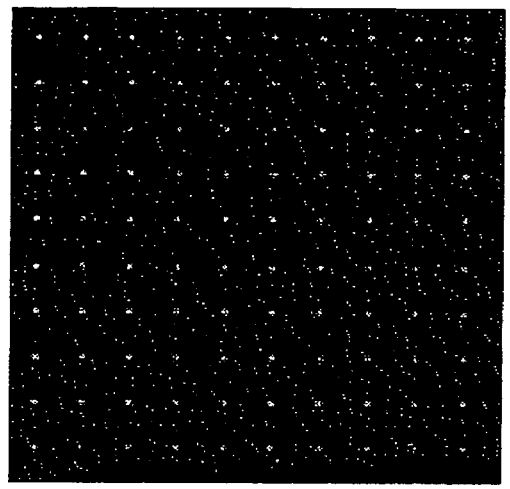
Figure 7C:
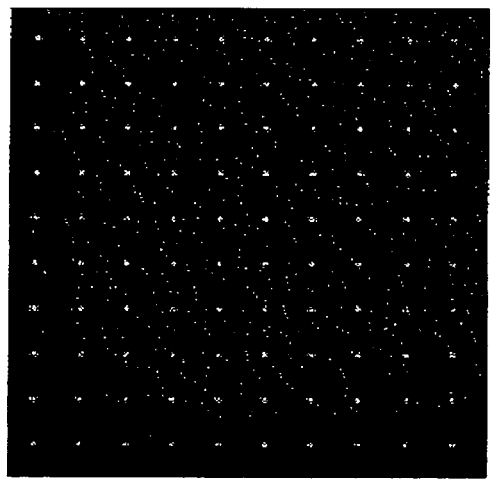
Figure 7D:
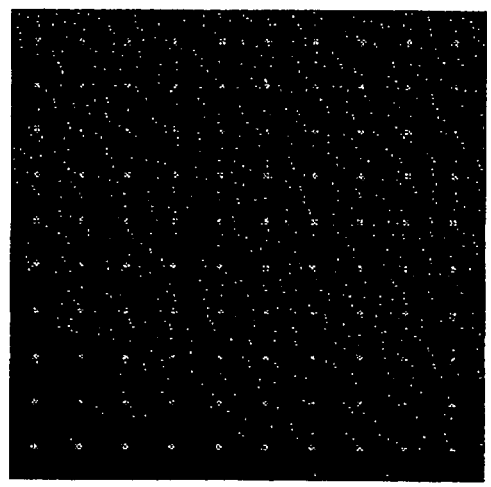
Figure 8A:
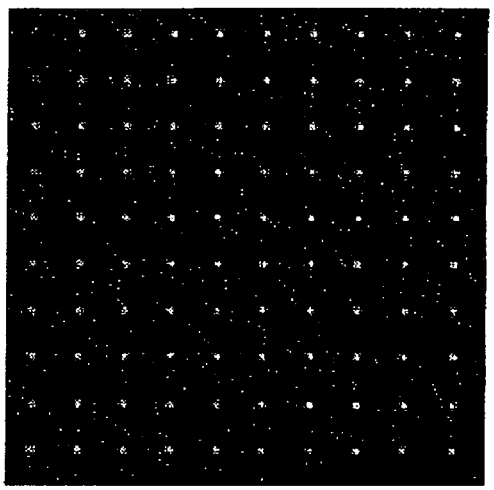
FIGS. 8A-D show a glass slide coated with 3-(N-styrylmethyl-2-aminoethylamino)propyltrimethoxysilane (from the HCl salt).
Figure 8B:
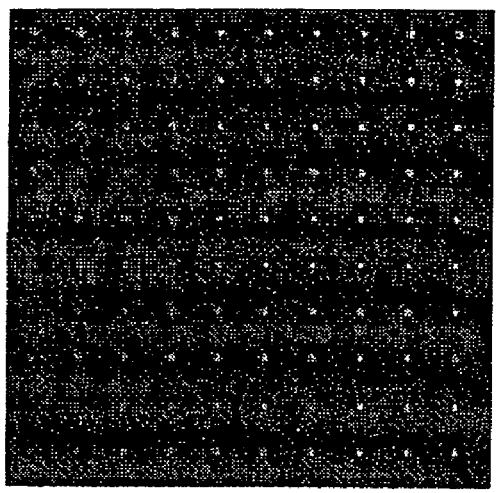
Figure 8C:
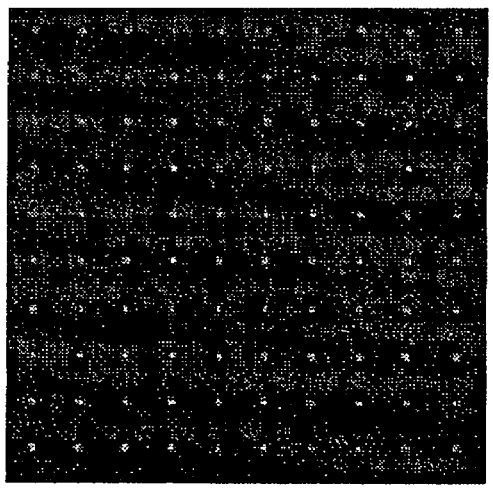
Figure 8D:
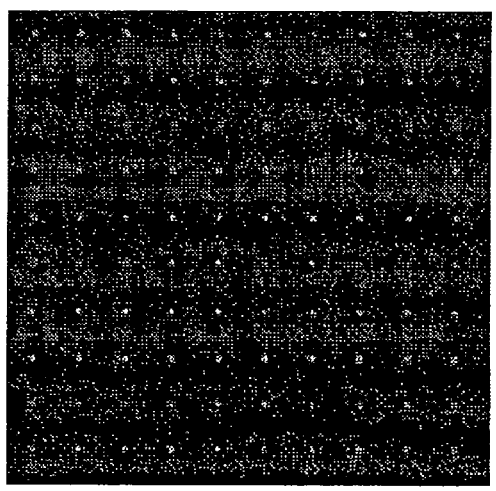
Figure 9A:
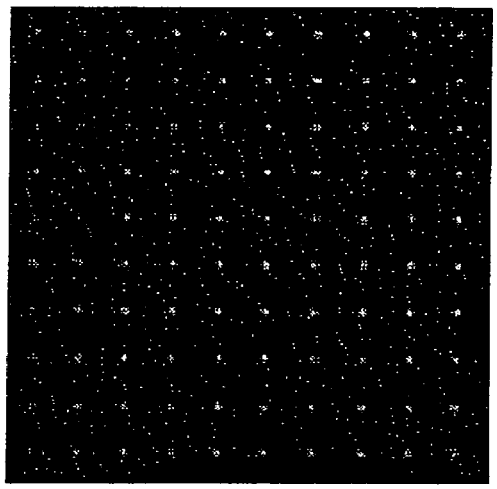
FIGS. 9A-F show a glass slide coated with N-(6-aminohexyl)aminopropyl trimethoxysilane.
Figure 9B:
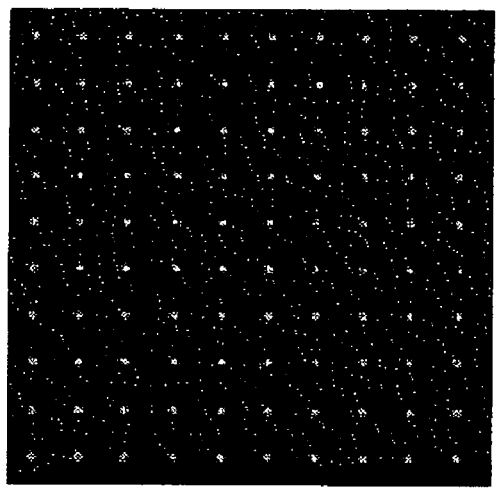
Figure 9C:
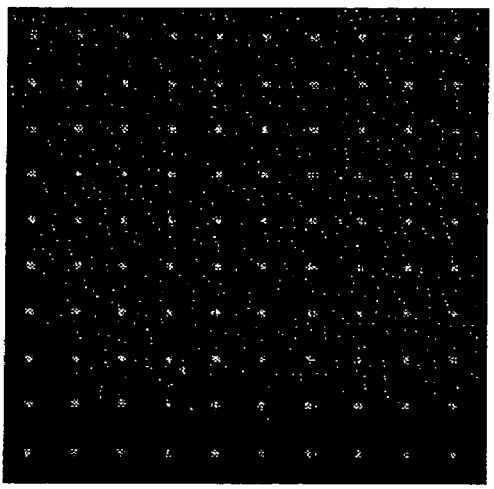
Figure 9D:
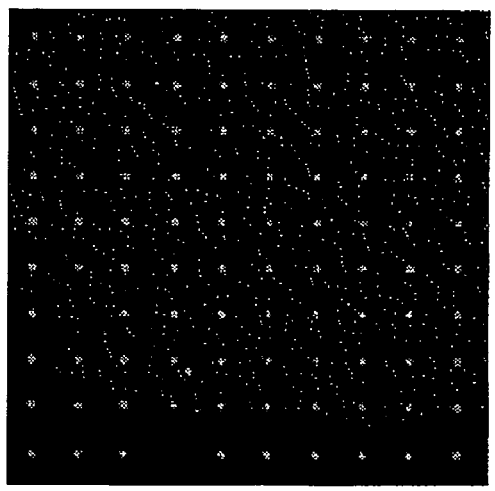
Figure 9E:
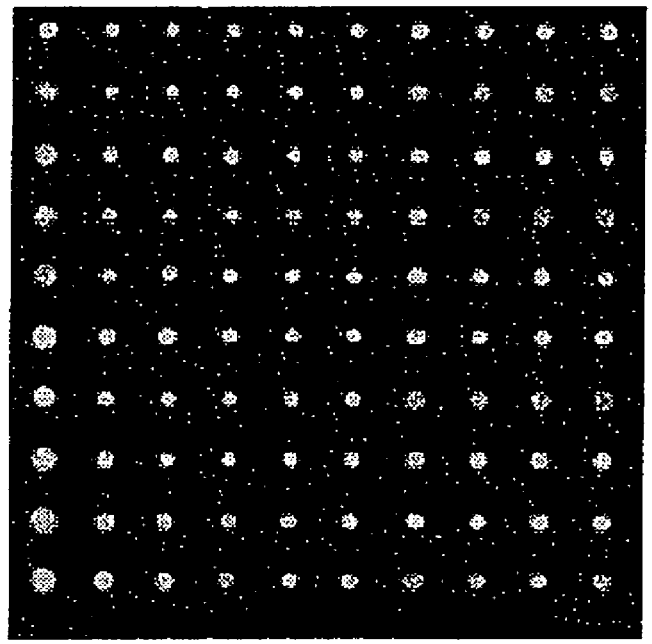
Figure 9F:
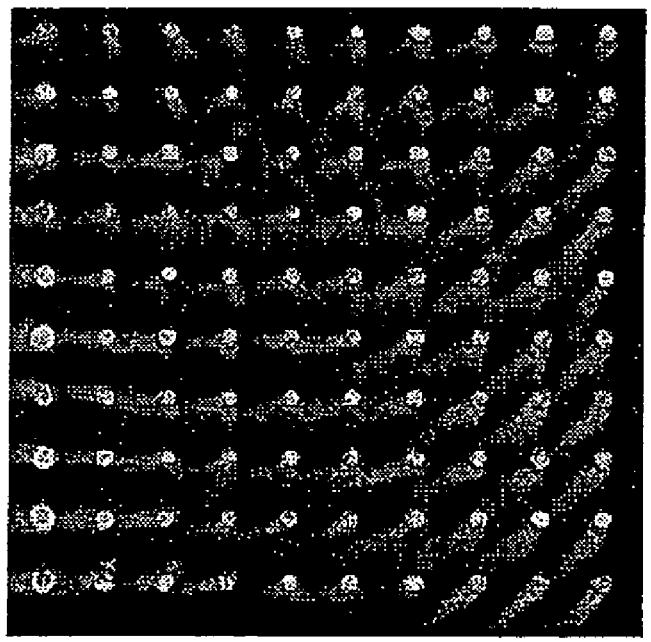

The use of amino compounds in the material and method of the present invention gives good binding efficiencies for biomolecules, e.g., DNA and proteins. The nature of the interaction is an electrostatic interaction with the positively charged amino surface (e.g., the negatively charged phosphate backbone of the DNA interacts with the positively charged amino surface). The amino surface is charged because of the formation of ammonium ions ($pK_a \sim 9$) when exposed to an aqueous solution. In accordance with the present invention, the overalkylating tendency of amino compounds is used to eliminate the possibility of the amine to react, thus preventing covalent bonding with DNA during a UV exposure. The quaternary ammonium ions can only participate in an elimination reaction to generate an alkene (Hoffman elimination) (March, *Advanced Organic Chemistry: Reactions. Mechanisms, and Structure*, Wiley, New York, p. 1016 (1992), which is hereby incorporated by reference in its entirety). Thus, it is not possible to form a covalent bond with anything one the amine is overalkylated. Another advantage of the overalkylated amine compounds in the material and method of the present invention is their stability. Where there is some degradation observed with primary amine surface (decreased signal in the gold colloid test), the materials of the present invention will not suffer from degradation. Overalkylating the amine also generates a positive charge on the molecule (and thus the surface) giving the desired electrostatic interaction with a biomolecule. In addition, as described above, the biomolecule retaining material of the present invention may use van der Waals interactions, in addition to ionic and dipole interactions, to bind biomolecules to the substrate. Examples of polyamino surfaces in accordance with this embodiment of the present invention are shown in FIG. 6, although other polyamino surfaces may be used.

Those skilled in the art, given the present description, will be able to identify and select suitable reagents depending on the type of biomolecule of interest.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments.

EXAMPLES

The invention will be further clarified by the following examples which are intended to be exemplary of the invention.

Example 1

A set of slides were prepared with trimethoxysilylpropyl ethylenediamine. The procedure for coating the slides consisted of: (1) a base pretreatment to clean and activate; (2) baking for one hour at 100° C. to remove adsorbed water; and (3) coating with a 3-5% solution in THF (tetrahydrofuran) for one hour, followed by a work-up. The slides were then further reacted with a 5% solution of methyl iodide for one hour to exhaustively methylate (overalkylate) all the amines (one primary and one secondary in the case of the diamine). This overalkylation produces two ammonium ions per molecule on the surface which means that there are two positive charges per molecule.

The viability of the surface was then tested by applying some DNA and subjecting the slide to the harshest step in the hybridization procedure, which is the denaturation step (two minutes in boiling water). The surface coated slide was printed with DNA (1.5 Kb) using the Flexys printer and scanned in the array scanner. The slide was then placed in boiling water for two minutes and scanned again to see if the DNA was still bound (electrostatically) to the surface. As was seen by viewing FIGS. 3A-D, some DNA remained bound to the slide (there was some loss due to the fact that excess DNA was printed). The S/N was low due to the smearing of the DNA in the absence of blocking material which was applied in the normal process to prevent non-specific binding of the hybridized DNA.

Example 2

A set of slides were prepared with $N^1$-[3-(trimethoxysilyl)propyl]ethylene diamine. The procedure for coating the slides consisted of: (1) a base pretreatment to clean and activate; (2) baking for one hour at 100° C. to remove adsorbed water; and (3) coating with a 3-5% solution in THF for one hour, followed by a work-up.

To test the viability of the surface coating it was printed and subjected to the harshest step in the hybridization procedure, which is the denaturation step. The surface coated slide was printed with DNA (1.5 Kb) using the Flexys printer and scanned in the array scanner. The slide was then placed in boiling water for two minutes and scanned again to see if the DNA was still bound (electrostatically) to the surface. As was seen by FIGS. 4A-D, some DNA still remained bound to the slide. There would of course be loss due to the fact that excess DNA was printed. The S/N was low due to the smearing of the DNA in the absence of blocking material which was applied in the normal process to prevent non-specific binding of the hybridized DNA.

Example 3

In this example, a surface coated with trimethoxysilylpropyl diethylenetriamine was modified by reacting it with trifluoroacetic anhydride. This surface was then printed with DNA (1.5 kDa) using Gen II ink (EG:water 80:20) and scanned. The slide was baked in an oven at 100° C. for three hours and then immersed in boiling water for two minutes, dried, and re-scanned. As can be seen from the data in Table 1 below, the contact angle of the triamine surface went from 40° to just over 70°.

TABLE 1

| Liquid | Solid | Right Angle | Left Angle | Average | Height | Width | Average |
|---|---|---|---|---|---|---|---|
| Slide #511 - Triamine | | | | | | | |
| D1 | Triamine | 38.5 | 40.7 | 39.6 | 0.02812 | 0.33047 | |
| D1 | Triamine | 43.1 | 37.0 | 40.0 | 0.03432 | 0.34618 | |
| D1 | Triamine | 43.9 | 41.2 | 42.5 | 0.03338 | 0.31969 | 40.8 |
| D1 | Triamine | 44.3 | 46.1 | 45.2 | 0.03914 | 0.33785 | |
| D1 | Triamine | 39.0 | 34.1 | 36.6 | 0.03383 | 0.34350 | |
| Slide #511 - Triamine modified with trifluoroacetic anhydride | | | | | | | |
| D1 | Triamine | 71.4 | 73.7 | 72.6 | 0.06532 | 0.25095 | |
| D1 | Triamine | 70.3 | 71.8 | 71.1 | 0.07006 | 0.27747 | |

TABLE 1-continued

| Liquid | Solid | Right Angle | Left Angle | Average | Height | Width | Average |
|---|---|---|---|---|---|---|---|
| D1 | Triamine | 70.4 | 71.7 | 71.0 | 0.05279 | 0.21708 | 71.8 |
| D1 | Triamine | 69.8 | 72.4 | 71.1 | 0.06509 | 0.25869 | |
| D1 | Triamine | 71.3 | 74.6 | 73.0 | 0.07225 | 0.27155 | |
| Slide #512 - Triamine | | | | | | | |
| D1 | Triamine | 42.2 | 40.6 | 41.4 | 0.02608 | 0.28274 | |
| D1 | Triamine | 44.6 | 33.3 | 38.9 | 0.03909 | 0.36847 | |
| D1 | Triamine | 42.1 | 39.6 | 40.8 | 0.03356 | 0.33337 | 39.9 |
| D1 | Triamine | 45.4 | 37.5 | 41.5 | 0.03405 | 0.31247 | |
| D1 | Triamine | 37.2 | 36.5 | 36.9 | 0.02327 | 0.28844 | |
| Slide #512 - Triamine modified with trifluoroacetic anhydride | | | | | | | |
| D1 | Triamine | 72.4 | 74.6 | 73.5 | 0.06516 | 0.24927 | |
| D1 | Triamine | 72.8 | 72.8 | 72.8 | 0.06759 | 0.25818 | |
| D1 | Triamine | 71.9 | 77.2 | 74.6 | 0.06875 | 0.26019 | 73.9 |
| D1 | Triamine | 71.5 | 73.9 | 72.7 | 0.06756 | 0.25909 | |
| D1 | Triamine | 75.3 | 76.8 | 76.1 | 0.06503 | 0.24667 | |
| Slide #513 - Triamine | | | | | | | |
| D1 | Triamine | 40.3 | 39.1 | 39.7 | 0.03455 | 0.33131 | |
| D1 | Triamine | 41.7 | 40.9 | 41.3 | 0.03719 | 0.34887 | |
| D1 | Triamine | 42.8 | 38.5 | 40.6 | 0.03455 | 0.33729 | 41.2 |
| D1 | Triamine | 42.0 | 41.9 | 41.9 | 0.03365 | 0.33665 | |
| D1 | Triamine | 43.6 | 41.1 | 42.3 | 0.03993 | 0.32662 | |
| Slide #513 - Triamine modified with trifluoroacetic anhydride | | | | | | | |
| D1 | Triamine | 72.7 | 73.5 | 73.1 | 0.07006 | 0.26280 | |
| D1 | Triamine | 74.6 | 77.9 | 76.3 | 0.06737 | 0.24985 | |
| D1 | Triamine | 73.2 | 79.3 | 76.2 | 0.06900 | 0.24725 | 76.4 |
| D1 | Triamine | 80.6 | 79.3 | 79.9 | 0.05063 | 0.18922 | |
| D1 | Triamine | 77.3 | 75.5 | 76.4 | 0.04684 | 0.18795 | |
| Slide #514 - Triamine | | | | | | | |
| D1 | Triamine | 38.9 | 35.9 | 37.4 | 0.04287 | 0.39220 | |
| D1 | Triamine | 36.1 | 36.4 | 36.3 | 0.03437 | 0.32609 | |
| D1 | Triamine | 36.2 | 35.8 | 36.0 | 0.03576 | 0.33547 | 38.0 |
| D1 | Triamine | 36.8 | 36.5 | 36.6 | 0.03666 | 0.32728 | |
| D1 | Triamine | 44.0 | 43.1 | 43.5 | 0.03918 | 0.33003 | |
| Slide #514 - Triamine modified with trifluoroacetic anhydride | | | | | | | |
| D1 | Triamine | 75.0 | 77.0 | 76.0 | 0.05905 | 0.22429 | |
| D1 | Triamine | 70.7 | 73.1 | 71.9 | 0.06631 | 0.25779 | |
| D1 | Triamine | 72.1 | 74.5 | 73.3 | 0.06388 | 0.24946 | 73.9 |
| D1 | Triamine | 74.5 | 76.5 | 75.5 | 0.06388 | 0.24446 | |
| D1 | Triamine | 69.4 | 76.2 | 72.8 | 0.06398 | 0.24686 | |

Figure 5A:
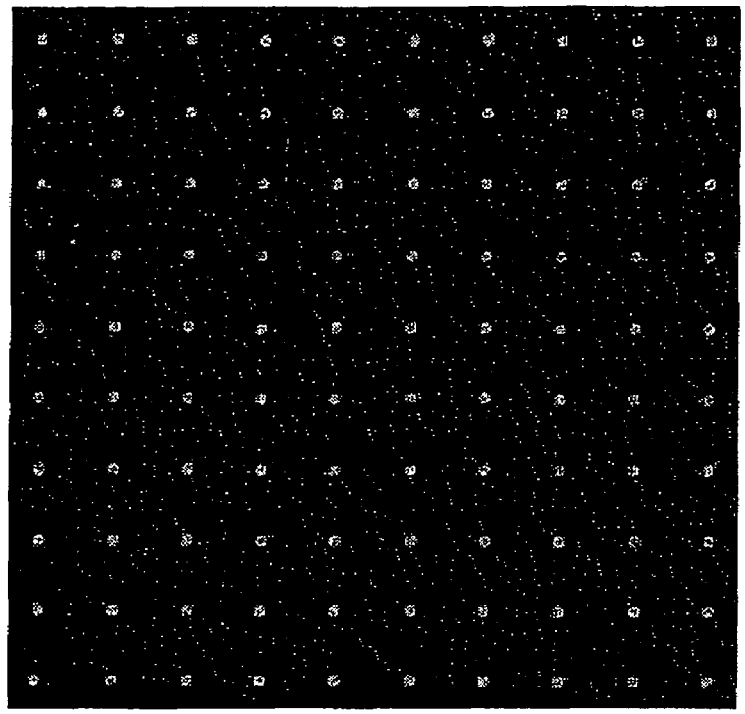
FIGS. 5A-B show a glass slide coated with trimethoxysilylpropyl diethylenetriamine and end-capped with a trifluoroacetyl group, printed with Gen II ink, baked for three hours at 100° C.
Figure 5B:
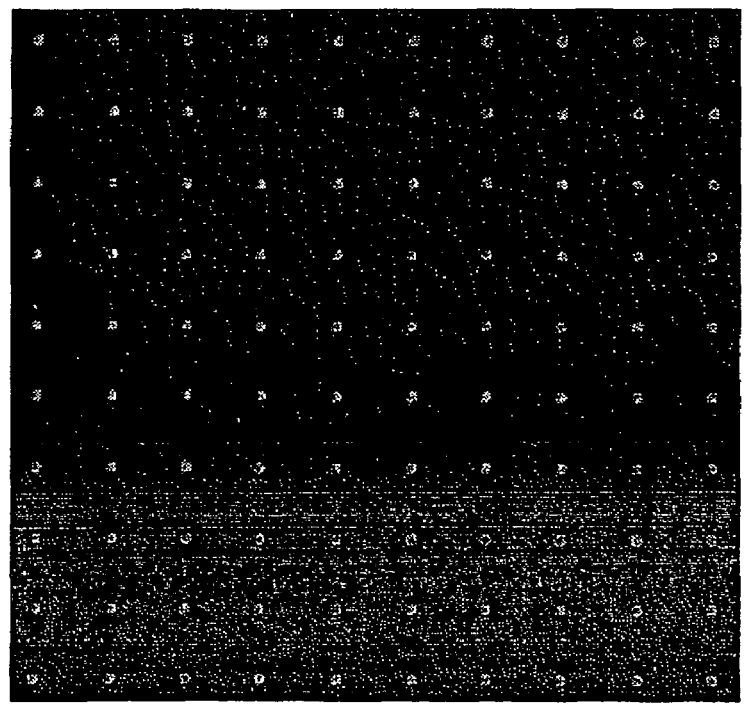

As shown in FIGS. 5A-B, the array remained intact with little spot migration, and the contact angle remained at over 70°.

This example describes the modification of the polyamine surface to meet the new desired attribute of a higher contact angle. The data shows a triamine surface modified to give an angle >70° while maintaining its superior ability to bind DNA.

Example 4

As illustrated above, the use of polyamine surfaces increases the bond density of the surface to give better retention, greater S/N, and low background fluorescence. The use of multiple modes can be extended beyond the polar/ionic functionality (phosphate) to include interactions with the bases.

It has been long known that the bases in DNA can stack upon each other due to the nature of the highly conjugated systems. This stacking phenomenon has been attributed to the conductivity of DNA in that electron transport is possible. These interactions are quite strong as illustrated by liquid crystals and the subsequent order induced. This ring-ring interaction (van der Waals interaction) can be another mechanism with which to bind DNA to the surface in concert with the ionic and dipole interactions. FIG. 6 illustrates three compounds that fall into this category of polyamino surfaces. Compounds 1-3 in FIG. 6 are: (aminoethylaminomethyl) phenethyl trimethoxysilane; N-(6-aminohexyl)aminopropyl trimethoxysilane; 3-(N-styrylmethyl-2-aminoethylamino) propyltrimethoxysilane (from the HCl salt), respectively. Compound 2 is a long chain polyamine but would still afford the van der Waals interaction.

FIGS. 7-9 show slides coated with compounds 1, 2, and 3 that include printing, boiling, and hybridization. As was seen from viewing the arrays in FIGS. 7-9, these surfaces give nice spot morphology and hybridization signal.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A biomolecule retaining material, comprising a substrate having a surface coated with a polyaminosilane compound on at least a portion of a surface of the substrate, wherein the polyaminosilane compound comprises a diamine or triamine, wherein at least one amine of the polyaminosilane compound is methylated or acetylated to produce a methylated or acetylated polyaminosilane compound, wherein the coated surface has a water contact angle greater than 46°.

2. The material of claim 1, further comprising a biomolecule non-covalently bound to the methylated or acetylated polyaminosilane compound.

3. The material of claim 2, wherein the biomolecule is DNA.

4. The material of claim 1, wherein the alkylated or acetylated polyaminosilane compound comprises $(OR^1)_3Si—CH_2(—[CH_2CH_2(NR^2)_n]_m$, wherein n is an integer from one to three, wherein m is an integer of three or greater, each $R^1$ is independently hydrogen or a lower alkyl having from one to four carbon atoms, and each $R^2$ is independently a hydrogen, a methyl group or an acyl group.

5. The material of claim 1, wherein the polyaminosilane compound comprises trialkoxysilylpropyl diethylenetriamine wherein at least one amine of the trialkoxysilylpropyl diethylenetriamine compound is methylated or acetylated to produce a methylated or acetylated polyaminosilane compound, wherein the coated surface has a water contact angle greater than 46°.

6. The material of claim 1, wherein at least one amine is over-alkylated.

7. The material of claim 1, wherein the substrate is glass.

8. A method of treating a biomolecule retaining material, comprising coating at least a portion of a substrate with a polyaminosilane compound and treating the polyaminosilane compound with an alkylating agent or acetylating agent to produce an alkylated or acetylated polyaminosilane compound suitable to increase the water contact angle of the coated substrate to greater than 46°, wherein at least one amine of the polyaminosilane compound is alkylated or acetylated.

9. The method of claim 8, wherein the alkylating agent comprises an alkyl halide.

10. The method of claim 8, wherein the acetylating agent comprises trifluoroacetic anhydride.

11. The method of claim 8, wherein the treating results in a coated substrate having a water contact angle greater than 70°.

12. The method of claim 8, wherein the treating results in a coated substrate having a water contact angle of from 50° to 80°.

13. The method of claim 8, wherein the polyaminosilane compound comprises a diamine.

14. The method of claim 8, wherein the polyaminosilane compound comprises a triamine.

15. The method of claim 8, wherein the alkylated or acetytated polyaminosilane compound comprises $(OR^1)_3Si-CH_2(-[CH_2CH_2(NR^2)_n]_m$, wherein n is an integer from one to three wherein m is an integer of two or greater, each $R^1$ is independently hydrogen or a lower alkyl having from one to four carbon atoms, and each $R^2$ is independently a hydrogen, a methyl group or an acyl group.

16. The method of claim 8, wherein the polyaminosilane compound comprises trialkoxysilylpropyl ethylenediamine.

17. The method of claim 8, wherein the polyaminosilane compound comprises trialkoxysilylpropyl diethylenetriamine.

18. The method of claim 8, further comprising over-alkylating at least one amine.

19. The method of claim 8, wherein the substrate is glass.

20. The method of claim 8, further comprising non-covalently binding a biomolecule to the coated substrate.

21. The method of claim 10, wherein the biomolecule is DNA.

22. The material of claim 1, wherein the coated substrate has a contact angle greater than 70°.

23. The material of claim 1, wherein the coated substrate has a contact angle of from 50° to 80°.

24. A material produced by the method of claim 8.

25. A biomolecule retaining material, comprising a glass substrate having a surface coated with a polyaminosilane compound on at least a portion of the surface of the glass substrate, wherein the polyaminosilane compound comprises a triamine, wherein at least one amine of the polyaminosilane compound is alkylated or acetylated to produce an alkylated or acetylated polyaminosilane compound, wherein the coated surface has a water contact angle greater than 46°.

26. The material of claim 25, further comprising a biomolecule non-covalently bound to the alkylated or acetylated polyaminosilane compound.

27. The material of claim 26, wherein the biomolecule is DNA.

28. The material of claim 25, wherein the alkylated or acetylated polyaminosilane compound comprises $(OR^1)_3Si-CH_2[CH_2CH_2(NR^2)_n]_m$, wherein n is an integer from one to three, wherein in is an integer of three or greater, each $R^1$ is independently hydrogen or a lower alkyl having from one to four carbon atoms, and each $R^2$ is independently a hydrogen, a methyl group or an acyl group.

29. The material of claim 25, wherein the polyaminosilane compound comprises trialkoxysilylpropyl diethylenetriamine.

30. The material of claim 25, wherein at least one amine is over-alkylated.

* * * * *

UNITED STATES PATENT AND TRADEMARK OFFICE
CERTIFICATE OF CORRECTION

PATENT NO.         : 7,541,146 B2                                         Page 1 of 1
APPLICATION NO. : 11/488557
DATED              : June 2, 2009
INVENTOR(S)        : Mark A. Lewis It is certified that error appears in the above-identified patent and that said Letters Patent is hereby corrected as shown below:

| Col. | Line | Description |
|------|------|-------------|
| 4  | 4  | Please delete "DESCRIPTIION" and add "DESCRIPTION" |
| 6  | 60 | Please delete after "angle" "for" and add "of" |
| 6  | 67 | Please delete after "way" "tat" and add "that" |
| 11 | 9  | Please delete "acetytated" and add "actylated" |
| 12 | 20 | Please delete after "wherein" "in" and add "m" |

Signed and Sealed this

First Day of September, 2009

David J. Kappos
*Director of the United States Patent and Trademark Office*